United States Patent
Belalcazar

[19]

[11] Patent Number: 6,016,446

[45] Date of Patent: Jan. 18, 2000

[54] CARDIAC RHYTHM MANAGEMENT SYSTEM INCLUDING NONLINEAR, NON-BLANKING SENSE AMPLIFIER

[75] Inventor: Hugo Andres Belalcazar, Bogota, Colombia

[73] Assignee: Cardiac Pacemakers, Inc., St. Paul, Minn.

[21] Appl. No.: 09/031,989

[22] Filed: Feb. 27, 1998

[51] Int. Cl.[7] .................................................. A61N 1/365
[52] U.S. Cl. .............................. 607/13; 607/9; 128/902; 600/509
[58] Field of Search .................................. 607/9, 17, 25, 607/13; 128/902, 901; 600/509

[56] References Cited

U.S. PATENT DOCUMENTS

| | | | |
|---|---|---|---|
| 3,898,994 | 8/1975 | Kolenik et al. .................... | 128/419 PG |
| 4,153,049 | 5/1979 | Gatzke et al. ............................... | 607/5 |
| 4,266,551 | 5/1981 | Stein ................... | 128/419 PG |
| 4,379,459 | 4/1983 | Stein et al. ......................... | 128/419 PG |
| 4,537,201 | 8/1985 | Delle-Vedove et al. ................ | 128/697 |
| 4,730,618 | 3/1988 | Lekholm et al. .................. | 128/419 PG |
| 4,960,123 | 10/1990 | Maker ......................................... | 607/4 |
| 5,018,523 | 5/1991 | Bach, Jr. et al. ....................... | 128/419 |
| 5,117,824 | 6/1992 | Keimel et al. ........................... | 128/419 |
| 5,330,512 | 7/1994 | Hauck et al. .............................. | 607/28 |
| 5,620,466 | 4/1997 | Haefner et al. .............................. | 607/5 |
| 5,683,431 | 11/1997 | Wang ......................................... | 607/28 |
| 5,718,242 | 2/1998 | McClure et al. ......................... | 600/515 |
| 5,755,738 | 5/1998 | Kim et al. .................................... | 607/9 |
| 5,843,136 | 12/1998 | Zhu et al. .................................. | 607/13 |

OTHER PUBLICATIONS

Horowitz, P., et al., *The Art of Electronics*, 2nd Edition, Cambridge University Press, p. 254, (1994).

*Primary Examiner*—William E. Kamm
*Assistant Examiner*—Kennedy J. Schaetzle
*Attorney, Agent, or Firm*—Schwegman, Lundberg, Woessner & Kluth, P.A.

[57] ABSTRACT

A cardiac rhythm management system provides a nonlinear gain characteristic. The system operates without blanking switches that decouple its inputs from electrodes during delivery of a pacing or recharge pulse. The nonlinear gain characteristic includes piecewise linear and logarithmic gain characteristics. Signals having amplitudes that are smaller than an input threshold voltage are amplified by less than signals having amplitudes that exceed the input threshold voltage. Intrinsic heart activity signals are amplified. Detected pacing pulses are attenuated. The system is capable of detecting an evoked response to determine whether a pacing pulse resulted in a successful heart contraction. Autocapture techniques allow adjustment of the pacing pulse energy based on the evoked response.

45 Claims, 9 Drawing Sheets

CARDIAC RHYTHM MANAGEMENT SYSTEM INCLUDING NONLINEAR, NON-BLANKING SENSE AMPLIFIER

TECHNICAL FIELD OF THE INVENTION

This invention relates generally to cardiac rhythm management systems, devices, and methods, and particularly, but not by way of limitation, to a cardiac rhythm management system that includes a nonlinear, non-blanking sense amplifier.

BACKGROUND OF THE INVENTION

Many techniques exist for treating abnormal cardiac rhythms ("arrhythmias") using cardiac rhythm management systems. For example, too-slow heart rhythms ("bradyarrhythmias" or "bradycardias") are readily treated by external or implantable pacemakers. Such pacers deliver pacing pulses to the heart to evoke a resulting electrical depolarization and accompanying heart contraction. By timing the delivery of pacing pulses, a patient's heart rhythm can be managed. In another example, too-fast heart rhythms ("tachycardias" or "tachyarrhythmias," including "fibrillation") are treated by external or implantable cardioverter/defibrillators (ICDs). Such ICD devices deliver timed pacing pulses to the heart to stabilize its rhythm or alternatively deliver an electrical countershock to interrupt fast electrical conduction paths causing the tachyarrhythmia.

Such cardiac rhythm management systems typically sense intrinsic heart activity signals that are produced by the heart itself Such intrinsic heart activity signals include the electrical depolarizations that cause heart contractions. These signals can be observed using surface electrocardiogram (ECG) equipment (i.e., using external electrodes for sensing intrinsic heart activity) or endocardial electrogram equipment (i.e., using electrodes disposed in the heart for sensing intrinsic heart activity). The cardiac rhythm management system typically bases delivery of therapy (e.g., pacing pulses or defibrillation countershocks) on particular heart rhythms appearing in the intrinsic heart activity signal.

Sensing intrinsic heart activity signals typically involves using a sense amplifier that is coupled to the heart via electrodes. For example, in an implantable pacemaker, an endocardial lead is transvenously introduced into the heart. The lead includes electrodes that are used for both sensing intrinsic heart activity signals and delivering pacing pulses. One known problem with using the same electrodes for both sensing and pacing is the buildup of residual electrical charge on the electrodes as a result of delivering the pacing pulse. Some of the residual charge may be removed by following the pacing pulse with an opposite polarity recharge pulse. Some residual charge, however, typically still exists even after the recharge pulse is delivered. The charge on the electrodes during the pacing and recharge pulses can overload ("saturate") the sense amplifier used for detecting intrinsic heart activity. The sense amplifier is not capable of detecting the intrinsic heart activity signal when the sense amplifier is in its saturated condition. Sense amplifiers may also unnecessarily consume more power when in a saturated condition.

In order to prevent the pacing pulse and accompanying residual charge from saturating the sense amplifier, the sense amplifier is typically "blanked," (i.e., decoupled from the electrodes by switches during the pacing pulses and during recharge time periods). The sense amplifier is reconnected to the electrodes shortly after the recharge pulse is delivered. Even using blanking techniques, several problems still exist. First, there remains some residual charge on the electrodes even when the sense amplifier is reconnected to the electrodes. This may cause a switch closure transient voltage on the heart activity signal sensed by the sense amplifier. Second, the sense amplifier is unable to provide information from the heart during the blanking time periods when it is disconnected. Losing information from the heart during blanking periods is particularly disadvantageous when managing fast cardiac rhythms (e.g., atrial flutter) because, for faster rhythms, more information is lost. Third, blanking techniques require additional components and control circuits, adding cost and complexity to the cardiac rhythm management system. There is a need for improved techniques for sensing heart activity and delivering pacing therapy to a patient.

SUMMARY OF THE INVENTION

In one embodiment, the present invention provides a first method. A sensed signal, which includes a heart activity component, is received from a heart. The sensed signal is nonlinearly amplified. Pacing pulses are delivered to the heart based on the heart activity component of the nonlinearly amplified sensed signal. The step of amplifying the sensed signal includes amplifying during time periods in which the pacing pulses are being delivered to the heart. In one embodiment, the method includes determining, based on the amplified sensed signal, whether the pacing pulse evoked a subsequent electrical depolarization of the heart. In another embodiment, the method includes adjusting the amplitude of the pacing pulses based on the step of determining whether the pacing pulse evoked a subsequent electrical depolarization of the heart.

In another embodiment, the invention provides a second method. A sensed signal, which includes a heart activity component, is received from a heart. The sensed signal is amplified by a first gain, if an amplitude of the sensed signal is approximately less than or equal to an input threshold voltage. The sensed signal is amplified by a second gain, which is less than the first gain, if the amplitude of the sensed signal approximately exceeds the input threshold voltage. Pacing pulses are delivered to the heart based on the heart activity component of the amplified sensed signal. In one embodiment, the method includes determining, based on the amplified sensed signal, whether the pacing pulse evoked a subsequent electrical depolarization of the heart. In another embodiment, the method includes adjusting the amplitude of the pacing pulses based on the step of determining whether the pacing pulse evoked a subsequent electrical depolarization of the heart.

Another aspect of the invention provides a first cardiac rhythm management system. The system includes first and second electrodes. A therapy module is coupled to the first and second electrodes for delivering pacing pulses to a heart. A sense amplifier is provided. The sense amplifier includes an input and an output. The input of the sense amplifier is coupled to the first and second electrodes for receiving a sensed signal including a heart activity component. The sense amplifier includes a nonlinear gain characteristic. The input of the sense amplifier is coupled to the first and second electrodes at least during time periods in which the pacing pulses are delivered to the heart. In one embodiment, the system includes an amplitude measurement module for measuring the amplitude of the pacing pulses. In another embodiment, the system includes an evoked response detection module. The evoked response detection module includes an input and an output. The input is coupled to the first and second electrodes. The evoked response detection module determines, based on the sensed signal, whether the pacing pulse evoked an electrical depolarization of the heart. In a further embodiment, the system includes an autocapture module for adjusting the amplitude of the pacing pulses based on the output of the evoked response detection module.

In another embodiment, the present invention provides a second cardiac rhythm management system. The system includes first and second electrodes. A therapy module is coupled to the first and second electrodes for delivering pacing pulses to a heart. The system also includes a sense amplifier. The sense amplifier includes an input and an output. The input of the sense amplifier is coupled to the first and second electrodes for receiving a sensed signal including a heart activity component. The sense amplifier includes a nonlinear gain characteristic. The nonlinear gain characteristic includes a first gain at amplitudes of the sensed signal that are less than or equal to an input threshold voltage, and a second gain, which is lower than this first gain, at amplitudes of the sensed signal that exceed the threshold voltage. In one embodiment, the system includes an amplitude measurement module for measuring the amplitude of the pacing pulses. In another embodiment, the system includes an evoked response detection module. The evoked response detection module includes an input and an output. The input is coupled to the first and second electrodes. The evoked response detection module determines, based on the sensed signal, whether the pacing pulse evoked an electrical depolarization of the heart. In a further embodiment, the system includes an autocapture module for adjusting the amplitude of the pacing pulses based on the output of the evoked response detection module.

The present invention provides, among other things, a cardiac rhythm management system, device, and methods including a nonlinear and/or non-blanking sense amplifier. The sense amplifier does not suffer from switch closure transient voltages resulting from operating blanking switches. The sense amplifier also provides information from the electrodes during delivery of pacing pulses and during recharge time periods. Such information is useful for, among other things, determining whether a pace pulse successfully resulted in a heart contraction, or for determining the amplitude of the delivered pacing pulse and the pacing impedance. Also, by avoiding blanking techniques, the present invention requires fewer components and components and control circuits, thereby reducing the cost, complexity, and power consumption of the cardiac rhythm management system. Other advantages will be apparent upon reading the following detailed description of the invention, together with the accompanying drawings which form a part thereof.

BRIEF DESCRIPTION OF THE DRAWINGS

In the drawings, like numerals describe substantially similar components throughout the several views.

DETAILED DESCRIPTION OF THE INVENTION

Figure 1A:
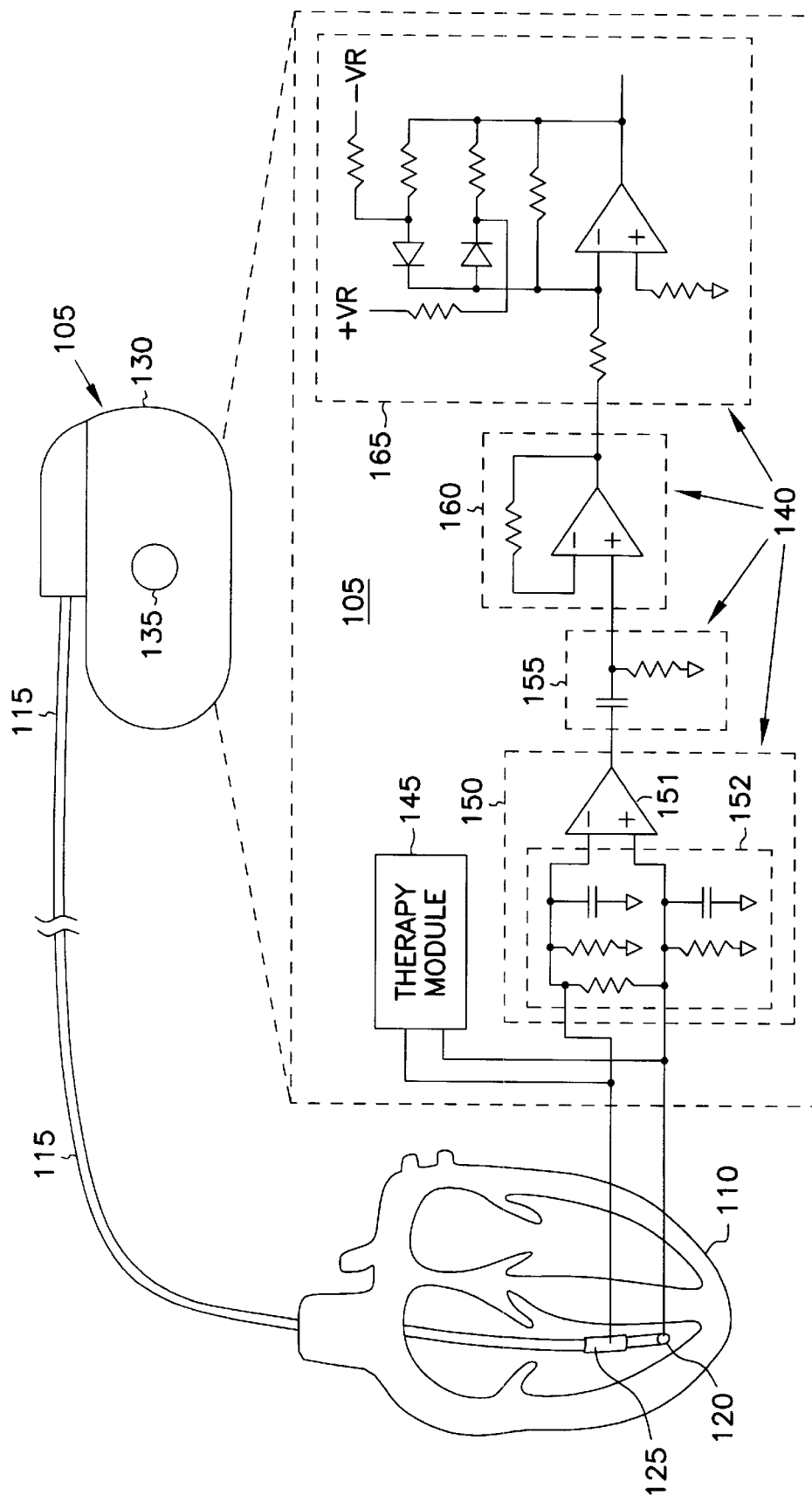
FIG. 1A is a generalized schematic illustration of one embodiment of a cardiac rhythm management system and the environment in which it is used.

In the following detailed description of the invention, reference is made to the accompanying drawings which form a part hereof, and in which is shown, by way of illustration, specific embodiments in which the invention may be practiced. In the drawings, like numerals describe substantially similar components throughout the several views. Exact sizes, shapes, and component values are not critical unless otherwise indicated in the accompanying description. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims, along with the full scope of equivalents to which such claims are entitled.

The present invention provides, among other things, a cardiac rhythm management system including a nonlinear and/or non-blanking sense amplifier. The sense amplifier senses electrical signals, including a heart activity component, also referred to as electrical heart signals. Such electrical heart signals include, among other things, the electrical depolarizations that cause heart contractions in the atrial and/or ventricular heart chambers (e.g, P-waves, QRS complexes, and T-waves), and are also referred to as "intrinsic heart activity signals," "electrocardiogram (ECG) signals," "ECG signals," and "electrogram signals." The sense amplifier does not suffer from switch closure transient voltages resulting from operating blanking switches. The sense amplifier also provides information from the electrodes during delivery of pacing pulses and during recharge time periods. Such information is useful for, among other things, determining whether a pace pulse successfully resulted in a heart contraction, or for determining the amplitude of the delivered pacing pulse or pacing impedance. Also, by avoiding blanking techniques, the present invention requires fewer components and components and control circuits, thereby reducing the cost, complexity, and power consumption of the cardiac rhythm management system.

FIG. 1A is a generalized schematic illustration of one embodiment of portions of the present invention, and the environment in which it is used. FIG. 1A illustrates a cardiac rhythm management system 100. System 100 includes, by way of example, but not by way of limitation, any system, implantable or external device, or method for sensing signals from a heart, or delivering therapy to manage the heart's rhythm. For example, in various embodiments, system 100 includes, but is not limited to: pacers, cardioverters, defibrillators, pacer/defibrillators, and drug delivery systems for cardiac rhythm management.

In the embodiment illustrated in FIG. 1A, system 100 includes, among other things, an implantable or external cardiac rhythm management device 105 that is coupled to a portion of a living organism, such as a heart 110, by a leadwire ("lead") 115. The terms "couple," "coupled," and "coupling" are broadly inclusive of any one or more of: a direct electrical connection, an indirect electrical connection, a capacitive connection, a communicative connection, and/or any other associative link. Embodiments of device 105 include bradycardia and antitachycardia pacers, cardioverters, defibrillators, combination pacer/defibrillators, drug delivery devices, and any other cardiac rhythm management apparatus capable of either sensing signals from or providing therapy to heart 110. System 100 may also include additional components such as, for example, a remote programmer capable of communicating with device 105.

In one embodiment, system 100 is implantable in the living organism, such as in a pectoral or abdominal region of a human patient, or elsewhere. In another embodiment, portions of system 100 (e.g., device 105) are alternatively disposed externally to the human patient. In the illustrated embodiment, portions of lead 115 are disposed in the right ventricle of heart 110, however, any other positioning of lead 115 in or near heart 110 is included within the present invention. For example, lead 115 may alternatively be positioned in the atrium or elsewhere. In one embodiment, lead 115 is a commercially available bipolar pacing lead. However, the present invention also includes unipolar embodiments. System 100 can also include other leads, in addition to lead 115, appropriately disposed, such as in or around heart 110, or elsewhere.

In one example, a first conductor of multiconductor lead 115 electrically couples a first electrode 120, such as a tip electrode disposed at the apex of the right ventricle of heart 110, to device 105. A second conductor of multiconductor lead 115 independently electrically couples a second electrode 125, such as a ring electrode disposed within the right ventricle of heart 110, to device 105. Device 105 includes a hermetically sealed housing 130, formed from a conductive metal, such as titanium. In a unipolar embodiment, housing 130 (also referred to as a "case" or "can") is substantially covered over its entire surface by a suitable insulator, such as silicone rubber, except for at a window that forms a third electrode, referred to as a "case" or "can" electrode 135. For this unipolar embodiment, can electrode 135 is substituted for one of first and second electrodes 120 and 125, such as for delivering pacing pulses and/or sensing intrinsic heart activity.

FIG. 1A also illustrates portions of device 105 in more detail. In one embodiment, for example, device 105 includes a sense amplifier 140 and a therapy module 145, each of which are coupled to first and second electrodes 120 and 125. Sense amplifier 140 receives intrinsic heart activity signals from heart 110 by sensing voltages that appear between first and second electrodes 120 and 125. In one embodiment, therapy module 145 delivers pacing pulses to heart 110, such as between first and second electrodes 120 and 125. In one example, therapy module 145 delivers pacing pulses based on the heart activity component of the sensed signal, for example, inhibiting delivery of the pacing pulses when intrinsic heart contractions are sensed. In one embodiment of the present invention, sense amplifier 140 is connected to first and second electrodes 120 and 125 without intervening blanking switches for isolating sense amplifier 140 from first and second electrodes 120 and 125 during delivery of pacing pulses and during recharge time periods. As a result, sense amplifier 140 is capable of amplifying during time periods in which pacing pulses are being delivered to the heart and during immediately following time periods (e.g., during recharge periods).

Figure 1B:
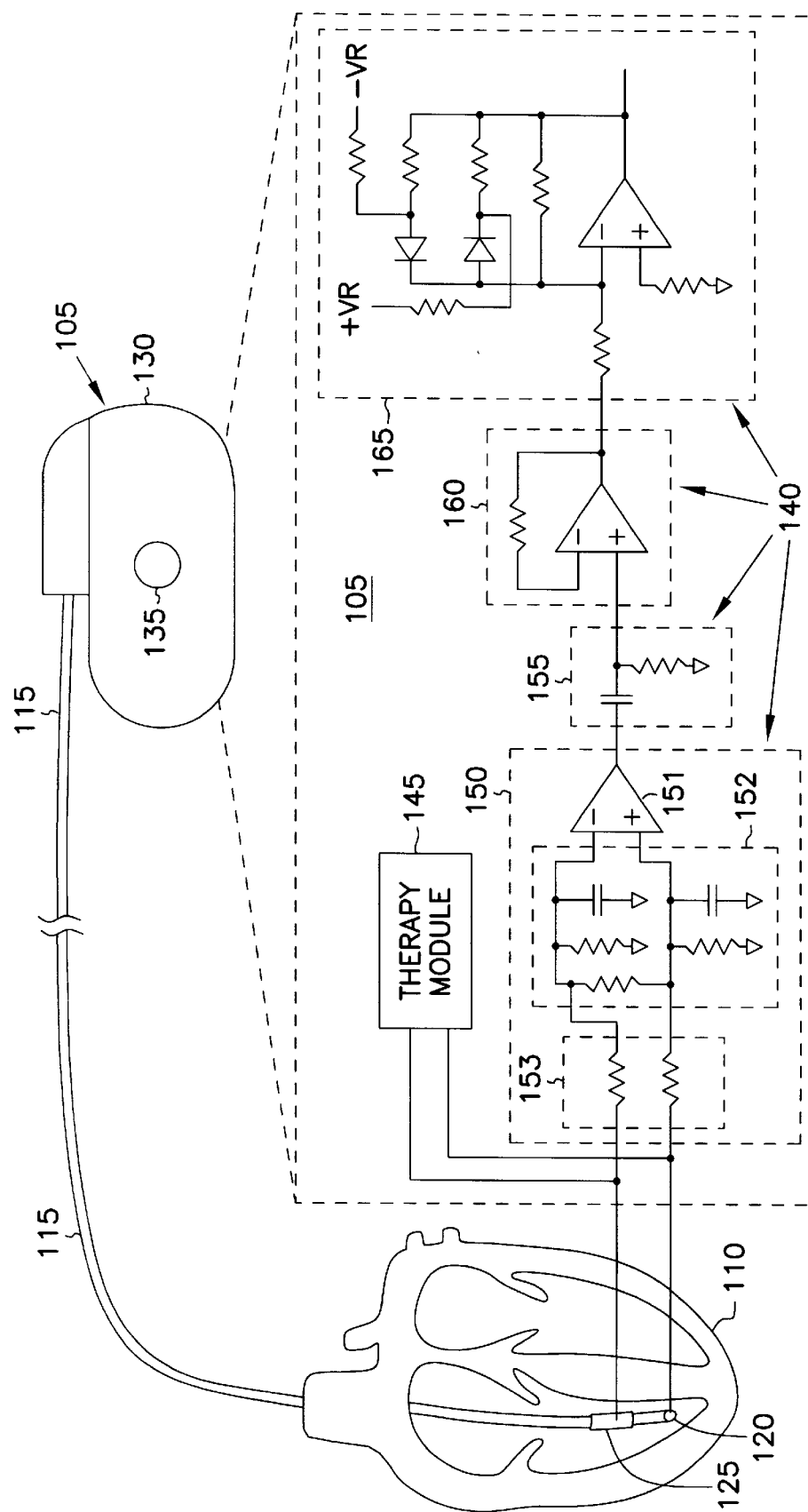
FIG. 1B, which is similar to FIG. 1A, includes an attenuation circuit.

In one embodiment, sense amplifier 140 includes front-end circuit 150, high pass filter 155, buffer 160, and amplifier 165. Front-end circuit 150 has inputs that are coupled to first and second electrodes 120 and 125 for receiving an electrical signal that includes an intrinsic heart activity signal component. Front-end circuit 150 removes any common mode signal received from first and second electrodes 120 and 125, such as by using an instrumentation amplifier 151, a differential amplifier, or by using other suitable techniques. In one embodiment, front-end circuit 150 also optionally includes filter circuit 152 for removing unwanted noise signals (e.g., for radio-frequency (RF) noise rejection). Filter circuit 152 is illustrated in FIG. 1A by way of example only, and not by way of limitation. Other topologies of filter circuit 152 could also be used, for example, replacing resistors with inductors to obtain higher order filter transfer functions. In one embodiment, front-end circuit 150 also includes an attenuation circuit 153, as illustrated in FIG. 1B. Attenuation circuit 153 forms a resistor divider (e.g., together with filter circuit 152) to avoid saturating amplifier 151 during delivery of pacing pulses having a higher amplitude than the power supply voltage of amplifier 151.

Front-end circuit 150 outputs a single-ended signal that is based on the signal received between tip first and second electrodes 120 and 125. In one embodiment, by way of example, but not by way of limitation, front-end circuit 150 provides a voltage gain of approximately 1.0. Because front-end circuit 150 does not provide high gain, it does not saturate during delivery of pacing pulses or during recharge time periods.

Sense amplifier 140 also includes, in one embodiment, a passive high pass filter 155, the input of which is coupled to receive the output of front-end circuit 150. High pass filter 155 removes components of the received electrical signals having frequencies that are below a cutoff frequency that is approximately between 9–40 Hz (e.g., approximately between 9–10 Hz). The cutoff frequency is selected to remove frequency components that are below the frequencies of interest in the intrinsic heart activity signal.

Buffer 160 includes, in one embodiment, a voltage follower amplifier configuration having an input that is coupled to high pass filter 155. Buffer 160 provides isolation between passive high pass filter 155 and amplifier 165, such that high pass filter 155 is not loaded by subsequent circuits, and amplifier 165 is adequately driven.

According to one aspect of the invention, amplifier 165 provides a nonlinear gain characteristic (e.g., logarithmic, piecewise linear, or other nonlinear gain characteristic). The term "gain" refers generally to both amplification and attenuation, and the terms "amplifying" and "amplification" are broadly inclusive of both attenuation and amplification. In one embodiment, amplifier 165 provides a first gain when its input voltage is small, and a second gain when its input voltage is large. The second gain is less than the first gain. As a result, smaller input signals are amplified more than larger input signals. One example of an amplifier having a nonlinear gain characteristic is described in P. Horowitz et al., "The Art of Electronics," Cambridge University Press, 2nd ed. 1989, p. 252.

Figure 2:
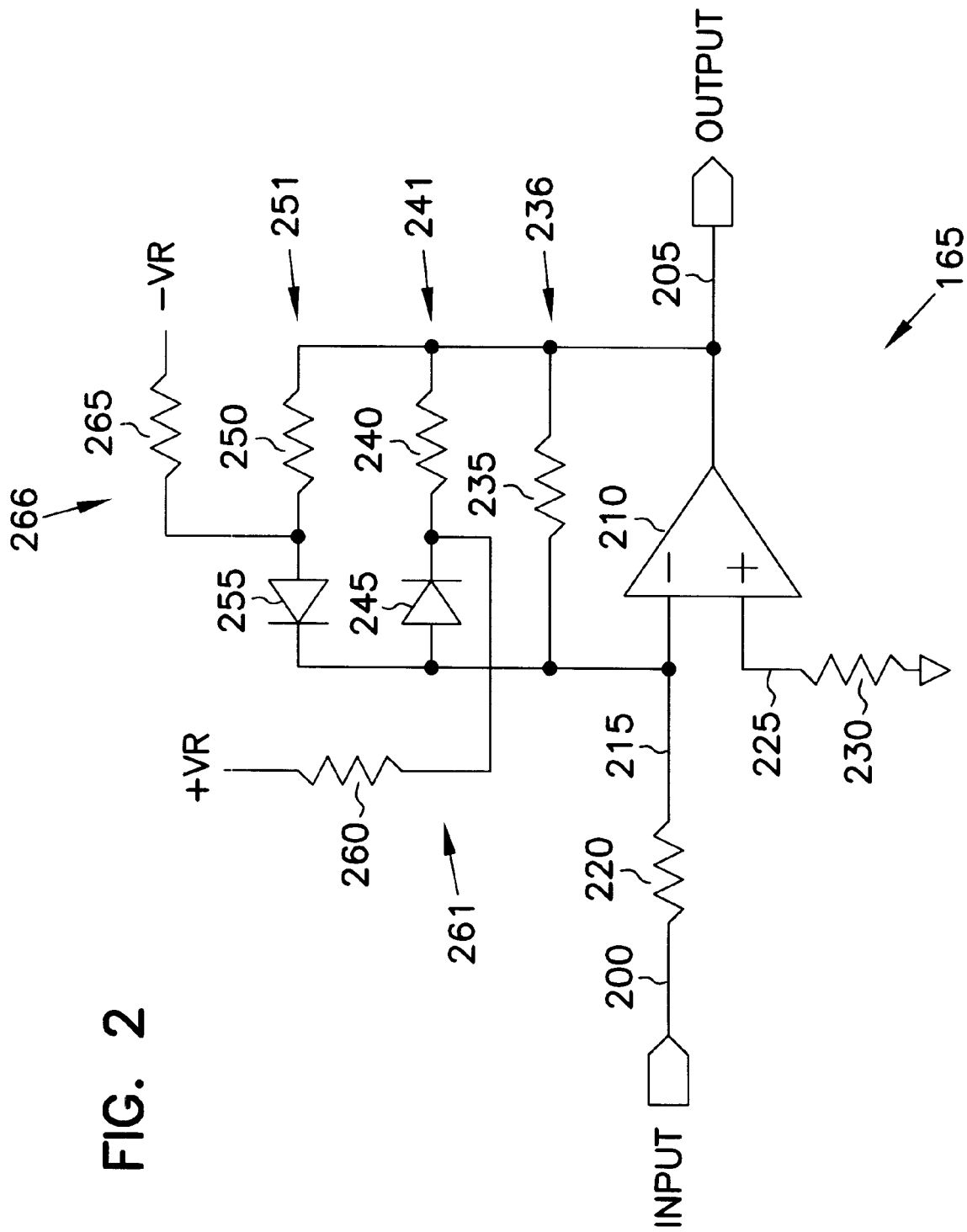
FIG. 2 is a schematic diagram illustrating generally one embodiment of portions of an amplifier.

FIG. 2 is a schematic diagram illustrating generally, by way of example, but not by way of limitation, one embodiment of portions of amplifier 165 having an input at node 200 and an output at node 205. Amplifier 165 includes an operational amplifier (op-amp) 210, or operational transconductance amplifier (OTA), or other suitable amplifier. Op-amp 210 has an inverting input that is coupled to a "virtual ground" node 215. Virtual ground node 215 is coupled to the input node 200 of amplifier 165 through a resistor 220. Op-amp 210 has a noninverting input, at node 225, coupled to a reference voltage, such as a ground voltage, through a resistor 230. Op-amp 210 has an output, at output node 205 of amplifier 165. The output of op-amp 210 is also fed back, through a first feedback path 236, to the inverting input of op-amp 210 at virtual ground node 215. First feedback path 236 includes a resistor 235.

In the embodiment of FIG. 2, amplifier 165 includes additional feedback paths between output node 205 and virtual ground node 215. A second feedback path 241 includes resistor 240 and diode 245. An anode terminal of diode 245 is coupled to virtual ground node 215. A cathode terminal of diode 245 is coupled output node 205 through resistor 240. A third feedback path 251 includes resistor 250 and diode 255. A cathode terminal of diode 255 is coupled to virtual ground node 215. An anode of diode 255 is coupled to output node 205 through resistor 250.

The embodiment of FIG. 2 also includes bias circuits for setting the operating point of diodes 245 and 255 which, in turn, establishes the circuit voltages at which second feedback path 241 and third feedback path 251 are conductive. For example, a first bias circuit 261 includes a resistor 260 coupling the cathode of diode 245 to a reference voltage (e.g., $+V_R$), such as the positive power supply voltage. In another example, a second bias circuit 266 includes a resistor 265 coupling the anode of diode 255 to a reference voltage (e.g., $-V_R$), such as the negative power supply voltage.

In operation, amplifier 165 provides signal amplification of the signal at input node 200, which includes an intrinsic heart activity signal. When the magnitude of the signal amplitude at input node 200 is below an input threshold voltage (also referred to as an input trip point voltage), amplifier 165 operates as an inverting amplifier, providing a first gain that is determined by first feedback path 236, as illustrated approximately by Equation 1.

$$\frac{v_{205}}{v_{200}} \approx -\frac{R_{235}}{R_{220}} \quad (1)$$

In Equation 1, $v_{205}$ is the voltage at output node 205, $v_{200}$ is the voltage at input node 200, $R_{235}$ is the resistance value of resistor 235, and $R_{220}$ is the resistance value of resistor 220.

Positive-going excursions of the signal at input node 200 result in negative-going excursions of the signal at output node 205. For positive-going excursions of the signal at input node 200 that exceed the input threshold voltage, diode 245 turns on, and the conductance of second feedback path 241 appears in parallel with the conductance of first feedback path 236. Diode 255 is off, making third feedback path 251 into an open circuit. When $R_{240} \ll R_{235}$, this provides a gain that is illustrated approximately by Equation 2.

$$\frac{v_{205}}{v_{200}} \approx -\frac{R_{240}}{R_{220}} \quad (2)$$

In Equation 2, $v_{205}$ is the voltage at output node 205, $V_{200}$ is the voltage at input node 200, $R_{240}$ is the resistance value of resistor 240, and $R_{220}$ is the resistance value of resistor 220.

Negative-going excursions of the signal at input node 200 result in positive-going excursions of the signal at output node 205. For negative-going excursions of the signal at input node 200 having a magnitude that exceeds the magnitude of an input threshold voltage, diode 255 turns on, and the conductance of third feedback path 251 appears in parallel with the conductance of first feedback path 236. Diode 245 is off, making second feedback path 241 into an open circuit. When $R_{250} \ll R_{R235}$, this provides a gain that is illustrated approximately by Equation 3.

$$\frac{v_{205}}{v_{200}} \approx -\frac{R_{250}}{R_{220}} \quad (3)$$

In Equation 3, $v_{205}$ is the voltage at output node 205, $v_{200}$ is the voltage at input node 200, $R_{250}$ is the resistance value of resistor 250, and $R_{220}$ is the resistance value of resistor 220.

Figure 3:
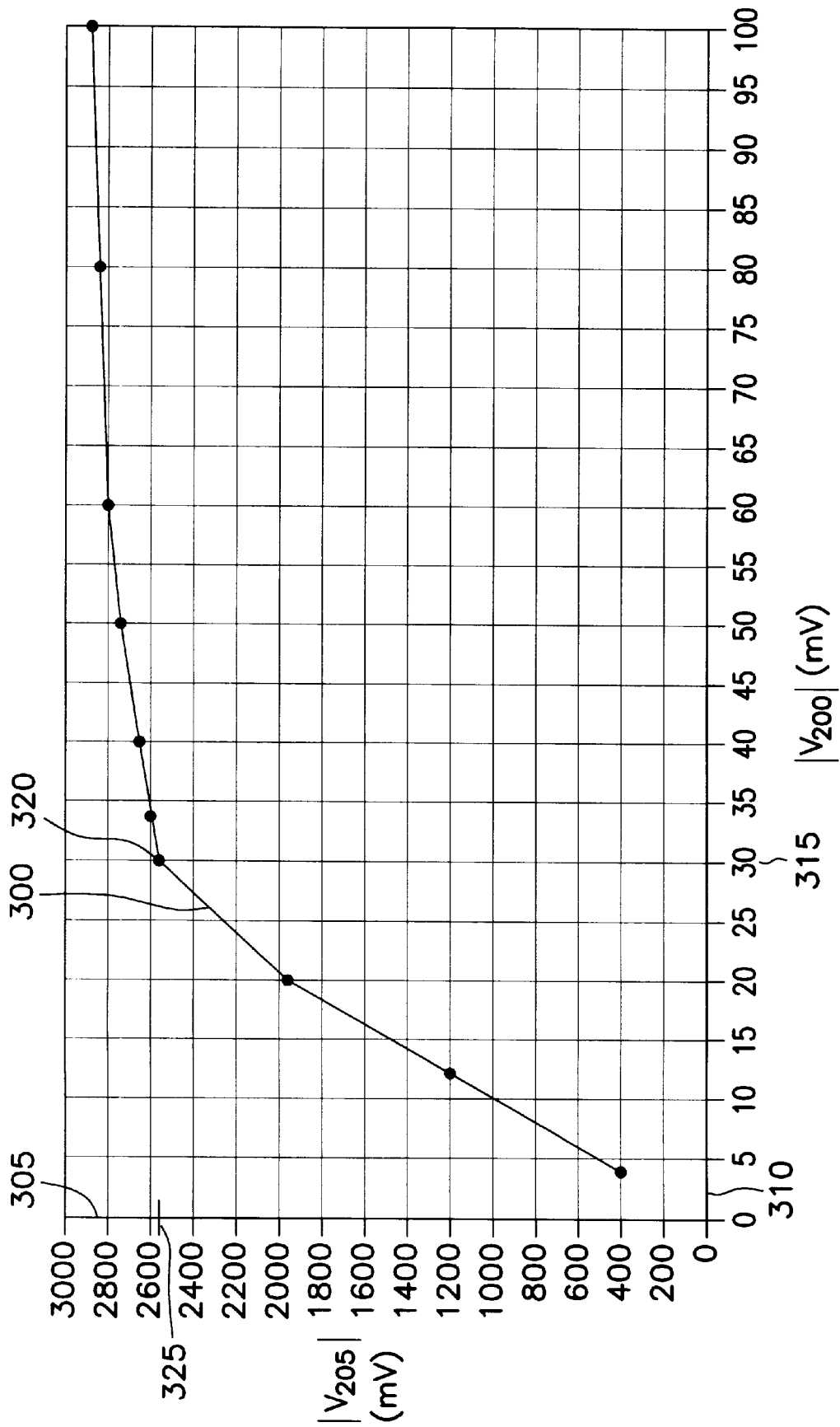
FIG. 3 is a graph illustrating generally a nonlinear transfer characteristic provided by one embodiment of an amplifier.

FIG. 3 is a graph illustrating generally, by way of example, but not by way of limitation, a nonlinear transfer characteristic 300 provided by one embodiment of amplifier 165. FIG. 3 includes a vertical axis 305, indicating the magnitude of output voltage $v_{205}$ at output node 205 in millivolts (mV). A horizontal axis 310 indicates the magnitude of input voltage $v_{200}$ at input node 200 in mV. In this embodiment, by way of example, but not by way of limitation, an input threshold voltage 315 of approximately 30 mV defines a breakpoint 320 between the two approximately linear segments of transfer characteristic 300, resulting in an approximately piecewise linear amplification. The 30 mV input threshold voltage 315 is illustrated in FIG. 3 by way of example only, and not by way of limitation. Many other values of the input threshold voltage 315 will be suitable. In general, the input threshold voltage 315 is selected such that intrinsic heart activity signals (e.g., having amplitudes approximately between 10 mV and 40 mV) are amplified by a high gain, and input signals resulting from a pacing pulse voltage (e.g., having amplitudes approximately between 0.4 V and 9.0 V) are either attenuated or amplified by only a very small gain. For example, if some degree of nonlinearity can be tolerated in the amplification of the intrinsic heart activity signal, the input threshold voltage 315 can be lowered from 30 mV to provide additional rejection of pacing pulse voltages. In generally, the input threshold voltage 315 should be smaller than the minimum pacing pulse voltage, so that the pacing pulse voltage is attenuated as illustrated in FIG. 3.

A trip point voltage $v_{325}$ at output node 205 for positive-going excursions of the input voltage $v_{200}$ at input node 200 is illustrated approximately by Equation 4 (neglecting the voltage drops across diodes 245 and 255).

$$v_{325} \approx \frac{R_{240}}{R_{260}} V_R \quad (4)$$

In Equation 4, $v_{325}$ is the trip point voltage at output node 205, $R_{240}$ is the resistance value of resistor 240, $R_{260}$ is the resistance value of the resistor 260, and $V_R$ is the value of the reference voltage to which resistor 260 is coupled. For an output voltage $v_{205}$ magnitude that is less than or equal to the trip point voltage $v_{325}$ magnitude of Equation 4, amplifier 165 provides the first gain illustrated by Equation 1. For an output voltage $v_{205}$ magnitude that exceeds the trip point voltage $v_{325}$ magnitude of Equation 4, amplifier 165 provides the second gain illustrated by Equation 2.

The trip point voltage $v_{325}$ can also be referred to input node 200, providing the input threshold voltage $v_{315}$ illustrated by Equation 5.

$$v_{315} \approx \frac{R_{240}}{R_{260}} \frac{R_{220}}{R_{235}} V_R \qquad (5)$$

In Equation 5, $v_{315}$ is the input threshold voltage at input node 200, $R_{240}$ is the resistance value of resistor 240, $R_{260}$ is the resistance value of the resistor 260, $R_{220}$ is the resistance value of resistor 220, $R_{235}$ is the resistance value of resistor 235, and $V_R$ is the value of the reference voltage to which resistor 260 is coupled. For negative-going excursions of the input voltage $v_{200}$ at input node 200, the trip point voltage $v_{325}$ at output node 205 and the input threshold voltage $v_{315}$ at input node 200 can be expressed by equations that are very similar to Equations 4 and 5.

In this embodiment, by way of example, but not by way of limitation, for input voltages $v_{200}$ that are less than or equal to the input threshold voltage $V_{315}$, amplifier 165 provides a first gain of approximately 100 Volts/Volt. For input voltages that exceed the input threshold voltage $V_{315}$, amplifier 165 provides a second gain that is less than the first gain such as, for example, but not by way of limitation, a second gain that is approximately 0.08. In this embodiment, the second gain is less than 1.0, providing attenuation of the input signal $v_{200}$ at input node 200. Many other values of the first and second gains are suitable for the present invention. In one embodiment, at least one of the first and second gains and the input threshold voltage is user programmable (e.g., remotely programmable in an implantable device). Selection of the first and second gains depends on many factors, including the gain and dynamic range available in other (e.g., subsequent) circuits, analog-to-digital (A/D) converter input voltage range, the particular power supply voltages used, etc.

Operation of this embodiment of amplifier 165 includes amplifying intrinsic heart activity signals (having low amplitudes of approximately between 0 mV and 30 mV, i.e., less than or equal to the input threshold voltage $v_{315}$), by a larger first gain, as illustrated in FIG. 3. Pacing pulses, recharge pulses, residual charge signals, or any other signals having amplitudes that exceed the input threshold voltage $v_{315}$ are amplified by the smaller second gain, as illustrated in FIG. 3, thereby avoiding saturation of amplifier 165 by such signals. As illustrated in the embodiment of FIG. 3, amplification by the smaller second gain also includes attenuation of signals exceeding the input threshold voltage $v_{315}$.

FIGS. 2 and 3 illustrate a particular embodiment of the invention in which amplifier 165 provides a piecewise linear transfer characteristic 300 that is approximately bilinear (i.e., having two approximately linear gain portions). However, the invention also includes other embodiments in which amplifier 165 provides other nonlinear transfer characteristics. For example, in one embodiment, the nonlinear transfer characteristic of amplifier 165 is piecewise linear with more than two approximately linear gain segments. In another example, the nonlinear transfer characteristic is approximately logarithmic. One example of an amplifier having an approximately logarithmic gain characteristic is described in P. Horowitz et al., "The Art of Electronics," Cambridge University Press, 2nd ed. 1989, p. 254.

Figure 4:
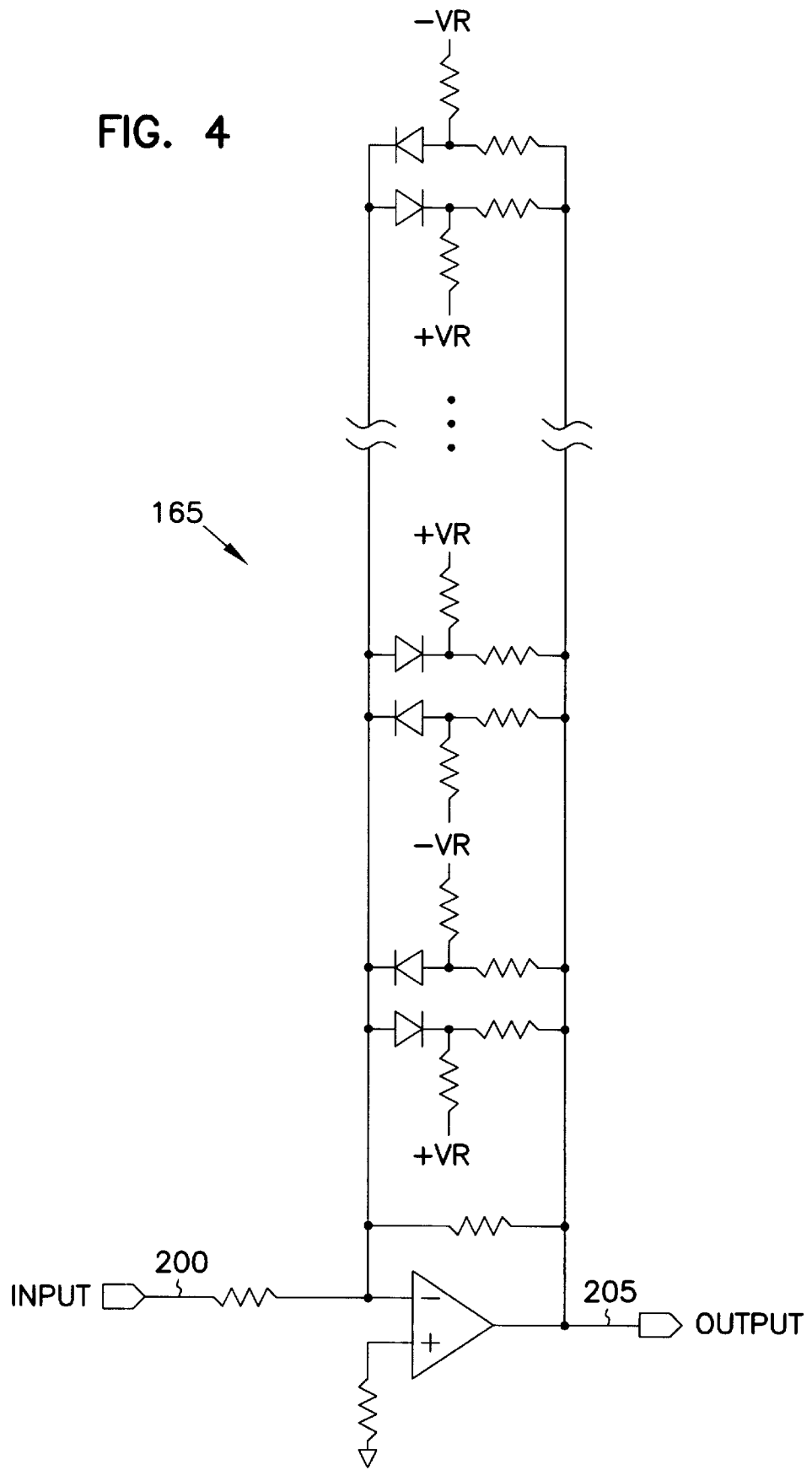
FIG. 4 is a schematic diagram illustrating generally one embodiment of an amplifier that provides a piecewise linear transfer characteristic including more than two approximately linear gain segments.
Figure 5:
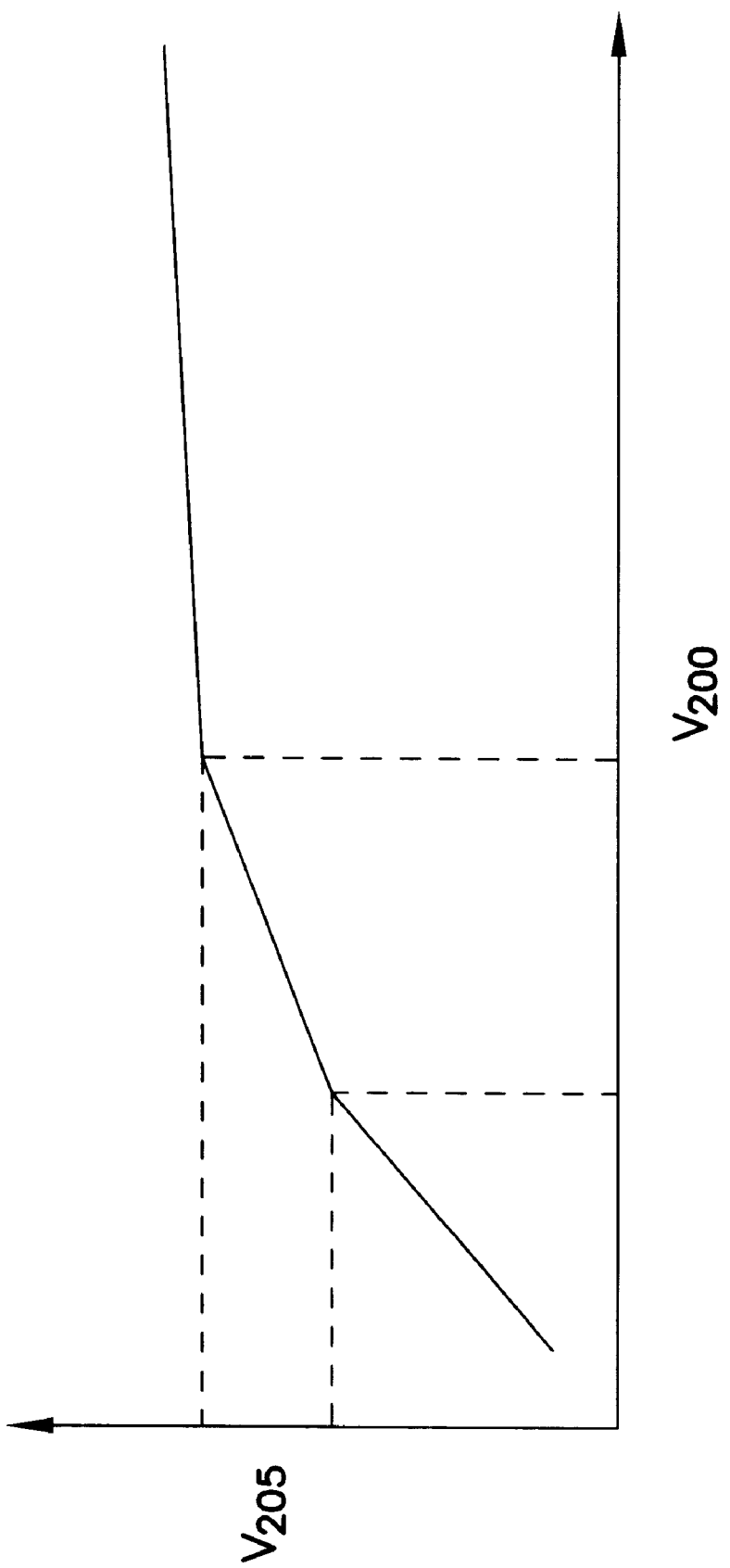
FIG. 5 is a graph illustrating generally a piecewise linear transfer characteristic including more than two approximately linear gain segments.

FIG. 4 is a schematic diagram, similar to FIG. 2, illustrating generally one embodiment of a amplifier 165 that provides a piecewise linear transfer characteristic including more than two approximately linear gain segments. In FIG. 4, additional parallel conductances are added into the feedback path in the manner described above with respect to FIG. 2. Power considerations may limit the number of additional parallel conductances that can be added. FIG. 5 is a graph illustrating generally, by way of example, a piecewise linear transfer characteristic including more than two (e.g., 3) approximately linear gain segments. Other circuit configurations and resulting nonlinear gain characteristics are also included within the present invention.

Evoked Response and Autocapture

Unlike conventional sense amplifiers, which typically use blanking switches to isolate the sense amplifier inputs from first and second electrodes 120 and 125 during delivery of pacing pulses and during recharge time periods, the inputs of sense amplifier 140 are coupled to first and second electrodes 120 and 125 at least during delivery of pacing pulses by therapy module 145 and during recharge time periods. In one embodiment, for example, sense amplifier 140 is always coupled to first and second electrodes 120 and 125.

Coupling sense amplifier 140 to first and second electrodes 120 and 125 without blanking advantageously eliminates switch closure transient voltages resulting from reconnecting sense amplifier inputs after blanking. Furthermore, this advantageously allows sense amplifier 140 to detect information from first and second electrodes 120 and 125 even during pacing pulses and recharge time periods. By contrast, conventional sense amplifiers using blanking switches do not provide information about heart activity from first and second electrodes 120 and 125 during the blanking periods when the sense amplifier is isolated therefrom.

Figure 6:
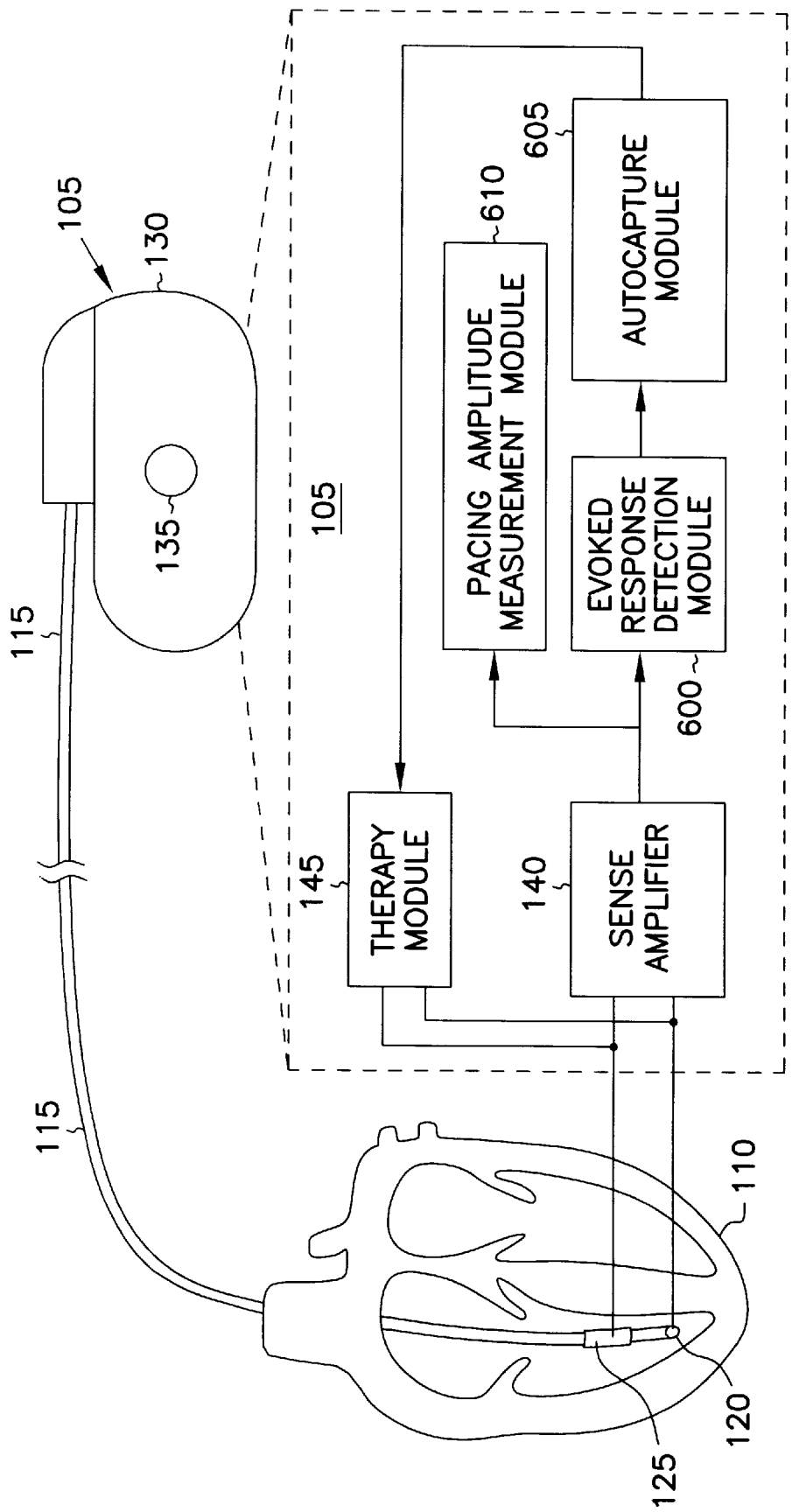
FIG. 6 is a block diagram illustrating generally a further embodiment of the present invention that uses information detected during and/or immediately after the delivery of the pacing pulses.

FIG. 6 is a block diagram illustrating generally a further embodiment of the present invention that uses information detected from first and second electrodes 120 and 125 during and/or immediately after the delivery of the pacing pulses. In one embodiment, device 105 of FIG. 6 includes an evoked response detection module 600 and an autocapture module 605. Evoked response detection module 600 includes circuits for detecting whether a particular pacing pulse delivered by therapy module 145 resulted in an electrical depolarization of heart 110 (referred to as the "evoked response" to the pacing stimulus) and accompanying contraction of heart 110. Examples of techniques used to detect evoked response is disclosed in Hauck et al. U.S. Pat. No. 5,330,512 entitled "ELECTRODE CHARGE-NEUTRAL SENSING OF EVOKED ECG," and Bach Jr. et al. U.S. Pat. No. 5,018,523 entitled "APPARATUS FOR COMMON MODE STIMULATION WITH BIPOLAR SENSING," each of which is assigned to the assignee of the present invention, and each of which are incorporated herein by reference.

Evoked response detection module 600 provides a digital output signal, indicating whether heart 110 was captured by the pacing pulse, to autocapture module 605. Autocapture module 605 is coupled to therapy module 145. Autocapture module 605 adjusts amplitude, pulsewidth, or other energy parameters of the pacing pulse delivered by therapy module 145 based on the input signal from evoked response detection module 605 indicating whether heart 110 was captured. Autocapture module 605 adjusts the energy of the pacing pulse to exceed the pacing stimulation threshold while minimizing the energy expended to obtain a successful resulting heart contraction. Since pacing stimulation thresholds may change over time, autocapture module 605 allows dynamic adjustment of the pacing pulse energy to ensure that the pacing pulses captures the heart. One example of autocapture techniques is described in Hauck et al. U.S. Pat.

No. 5,330,512 entitled "ELECTRODE CHARGE-NEUTRAL SENSING OF EVOKED ECG," which is incorporated herein by reference. The present invention, however, advantageously allows application of autocapture techniques using the same electrodes for both pacing and sensing the evoked response, thereby eliminating the need for sensing evoked response via special electrodes.

Figure 7:
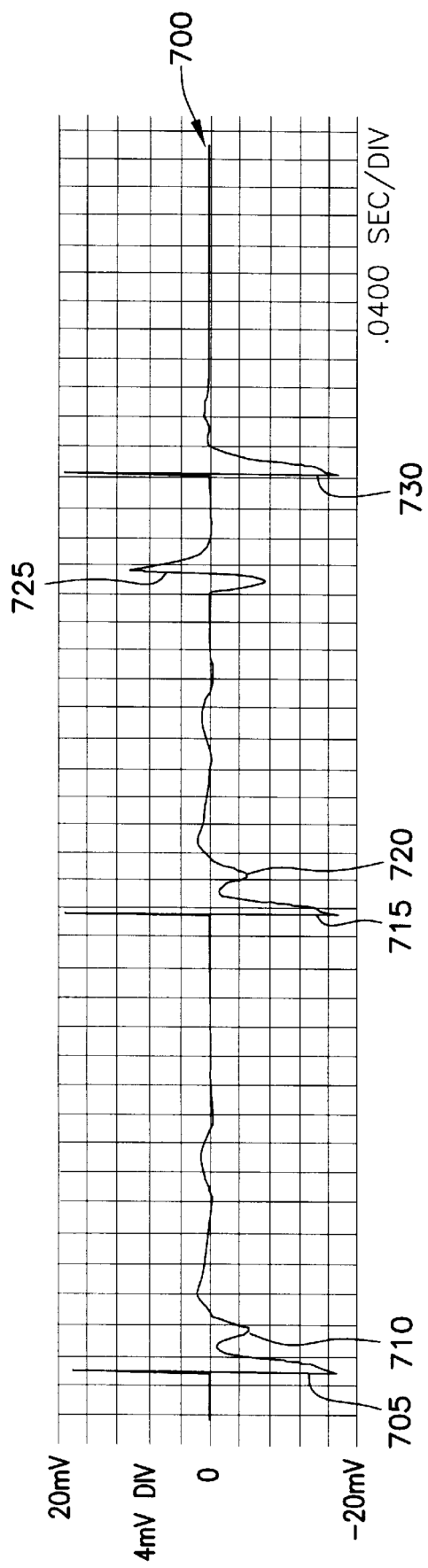
FIG. 7 is a graph illustrating generally a first electrogram signal that was obtained from a dog.

FIG. 7 is a graph illustrating generally an electrogram signal that was obtained from a dog using a cardiac rhythm management system 100. The electrogram signal was acquired through a non-blanking, nonlinear sense amplifier 140 coupled to the same first and second electrodes 120 and 125 that were used for delivering pacing pulses. Pacing pulse 705 was immediately followed by an easily discernable subsequent evoked response 710 indicating a successful heart contraction in response to pacing pulse 705. Similarly, pacing pulse 715 was also immediately followed by an easily discernable subsequent evoked response 720 indicating a successful heart contraction in response to pacing pulse 715. An intrinsic heartbeat (i.e., not initiated by a pacing pulse) is indicated by QRS complex 725. Subsequent pacing pulse 730 is not followed by an evoked response. The absence of an evoked response to pacing pulse 730 indicates that the heart was not "captured," i.e., pacing pulse 730 did not induce a successful heart contraction.

Figure 8:
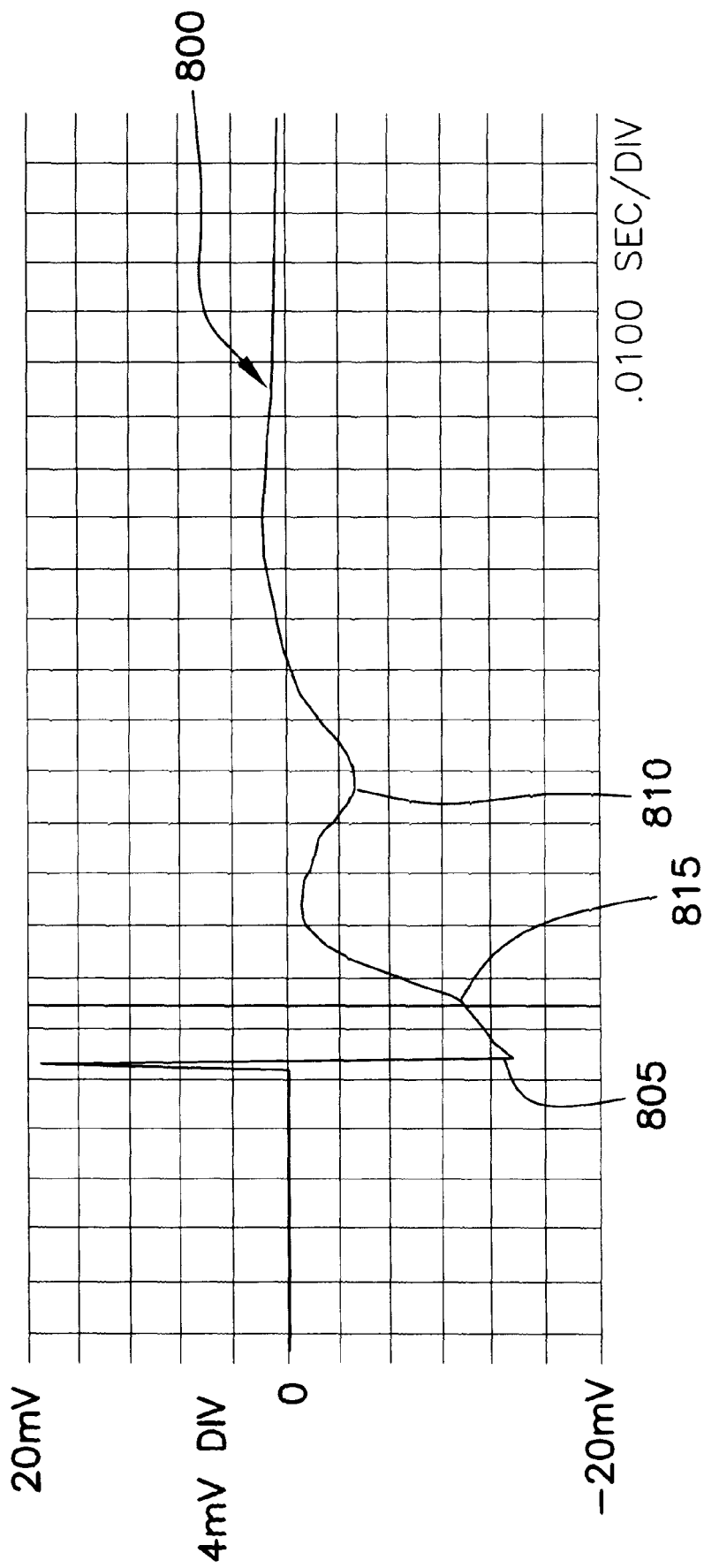
FIG. 8 is a graph illustrating generally a second electrogram signal that was obtained from a dog.

FIG. 8 is a graph, similar to FIG. 7, illustrating in more detail an electrogram 800 including a pacing pulse 805 and evoked response 810 acquired through sense amplifier 140. At time 815 (approximately 12 milliseconds after initiation of the delivery of pacing pulse 805) amplifier 165 ceases attenuating the pacing pulse 800 using the second gain and switches over to amplifying the intrinsic heart activity signal using the first gain, thereby obtaining the easily discernable evoked response 810.

Thus, by eliminating the use of blanking periods, sense amplifier 140 provides accurate information about heart activity, including evoked response information, which can be used to determine whether the pacing pulse successfully initiated a heart contraction. According to one aspect of the invention, the evoked response information is used by autocapture module 605 to adjust the pacing energy to a minimum value that still results in a successful heart contraction. This saves energy and, in a battery-powered implantable application, prolongs the useful life of cardiac rhythm management device 105.

Referring again to FIG. 6, in one embodiment, device 105 includes a pacing amplitude measurement module 610. Sense amplifier 140 is coupled to first and second electrodes 120 and 125 during delivery of pacing pulses, rather than being isolated therefrom by blanking switches. As a result, device 105 is capable of measuring the actual amplitude of the pacing pulse delivered between first and second electrodes 120 and 125 by monitoring the output of sense amplifier 140. In one embodiment, for example, this pacing pulse amplitude information is used to determine the lead impedance between first and second electrodes 120 and 125, such as to determine whether lead 115 is properly placed within heart 110 and effectively delivering pacing therapy.

Conclusion

As described above, the present invention provides, among other things, a cardiac rhythm management system including a nonlinear and/or non-blanking sense amplifier. The sense amplifier does not suffer from switch closure transient voltages resulting from operating blanking switches. The sense amplifier also provides information from the electrodes during delivery of pacing pulses and during recharge time periods. Such information is useful for, among other things, determining whether a pace pulse successfully resulted in a heart contraction, or for determining the amplitude of the delivered pacing pulse. Also, by avoiding blanking techniques, the present invention requires fewer components and components and control circuits, thereby reducing the cost and complexity of the cardiac rhythm management system.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:
receiving a sensed signal, which includes a heart activity component, from a heart;
nonlinearly amplifying the sensed signal;
delivering pacing pulses to the heart based on the heart activity component of the nonlinearly amplified sensed signal; and
wherein amplifying the sensed signal includes amplifying during time periods in which the pacing pulses are being delivered to the heart.

2. The method of claim 1, in which amplifying the sensed signal includes an approximately piecewise linear amplifying of the sensed signal.

3. The method of claim 1, in which amplifying the sensed signal includes an approximately logarithmic amplifying of the sensed signal.

4. The method of claim 1, in which amplifying the sensed signal includes amplifying during time periods immediately following the time periods in which the pacing pulses are being delivered to the heart.

5. The method of claim 1, in which amplifying the sensed signal includes amplifying during recharge time periods following the time periods in which the pacing pulses are being delivered to the heart.

6. The method of claim 1, further including determining, based on the amplified sensed signal, whether the pacing pulse evoked a subsequent electrical depolarization of the heart.

7. The method of claim 6, further comprising adjusting the amplitude of the pacing pulses based on the step of determining whether the pacing pulse evoked a subsequent electrical depolarization of the heart.

8. The method of claim 1, in which amplifying the sensed signal includes attenuating a component of the sensed signal.

9. A method comprising:
receiving a sensed signal, which includes a heart activity component, from a heart;
amplfying the sensed signal by a first gain if an amplitude of the sensed signal is approximately less than or equal to an input threshold voltage;
amplifying the sensed signal by a second gain, which is less than the first gain, if the amplitude of the sensed signal approximately exceeds the input threshold voltage; and
delivering pacing pulses to the heart based on the heart activity component of the amplified sensed signal.

10. The method of claim 9, in which amplifying the sensed signal by a first gain includes amplifying by approximately 100 when the amplitude of the sensed signal is approximately less than or equal to the input threshold voltage of approximately 30 milliVolts.

11. The method of claim 9, in which amplifying the sensed signal by a second gain includes amplifying by approximately 0.08 when the amplitude of the sensed signal approximately exceeds the input threshold voltage of approximately 30 milliVolts.

12. The method of claim 9, in which the steps of amplifying the sensed signal by first and second gains include amplifying during time periods immediately following the time periods in which the pacing pulses are being delivered to the heart.

13. The method of claim 9, in which the steps of amplifying the sensed signal by first and second gains include amplifying during recharge time periods following the time periods in which the pacing pulses are being delivered to the heart.

14. The method of claim 9, further comprising determining, based on the amplified sensed signal, whether the pacing pulse evoked a subsequent electrical depolarization of the heart.

15. The method of claim 14, further comprising adjusting the amplitude of the pacing pulses based on the step of determining whether the pacing pulse evoked a subsequent electrical depolarization of the heart.

16. The method of claim 9, further comprising programming a value of at least one of the input threshold voltage, the first gain, and the second gain.

17. The method of claim 9, in which at least one of amplifying the sensed signal by a first gain and amplifying the sensed signal by a second gain includes attenuating a component of the sensed signal.

18. A cardiac rhythm management system comprising:
first and second electrodes;
a therapy module, coupled to the first and second electrodes for delivering pacing pulses to a heart; and
a sense amplifier, including an input and an output, the input coupled to the first and second electrodes for receiving a sensed signal including a heart activity component, the sense amplifier having a nonlinear gain characteristic, wherein the input of the sense amplifier is coupled to the first and second electrodes at least during time periods in which the pacing pulses are delivered to the heart.

19. The system of claim 18, in which the nonlinear gain includes a first gain at amplitudes of the sensed signal that are less than or equal to an input threshold voltage and, at amplitudes of the sensed signal that exceed the input threshold voltage, a second gain that is lower than the first gain.

20. The system of claim 18, in which the nonlinear gain is approximately piecewise linear.

21. The system of claim 20, in which the nonlinear gain includes a first gain of approximately 100 for input voltages that are below an input threshold voltage of approximately 30 milliVolts, and the nonlinear gain includes a second gain of approximately 0.08 for input voltages that are above the input threshold voltage.

22. The system of claim 21, in which at least one of the first gain, the second gain, and the input threshold voltage is programmable.

23. The system of claim 18, in which the nonlinear gain is approximately logarithmic.

24. The system of claim 18, in which the sense amplifier is coupled to the first and second electrodes including during time periods immediately after the time periods during which the pacing pulses are delivered to the heart.

25. The system of claim 18, in which the sense amplifier is coupled to the first and second electrodes including during recharge time periods following the time periods during which the pacing pulses are delivered to the heart.

26. The system of claim 18, further comprising an amplitude measurement module, coupled to the first and second electrodes for measuring the amplitude of the pacing pulses.

27. The system of claim 18, further including an evoked response detection module having an input and an output, the input coupled to the first and second electrodes, the evoked response detection module determining, based on the sensed signal, whether the pacing pulse evoked an electrical depolarization of the heart.

28. The system of claim 27, further comprising an autocapture module coupled the evoked response detection module and the therapy module for adjusting the amplitude of the pacing pulses based on the output of the evoked response detection module.

29. The system of claim 18, in which the sense amplifier is always coupled to the first and second electrodes.

30. The system of claim 18, in which the sense amplifier is directly connected to the first and second electrodes.

31. A cardiac rhythm management system comprising:
first and second electrodes;
a therapy module, coupled to the first and second electrodes for delivering pacing pulses to a heart; and
a sense amplifier, including an input and an output, the input coupled to the first and second electrodes for receiving a sensed signal including a heart activity component, the sense amplifier having a nonlinear gain characteristic that includes a first gain at amplitudes of the sensed signal that are less than or equal to an input threshold voltage, and a second gain, which is lower than this first gain, at amplitudes of the sensed signal that exceed the threshold voltage.

32. The system of claim 31, in which the nonlinear gain is approximately piecewise linear.

33. The system of claim 31, in which the nonlinear gain is approximately logarithmic.

34. The system of claim 31, in which the first gain is approximately 100.

35. The system of claim 31, in which the input threshold voltage is approximately 30 milliVolts.

36. The system of claim 31, in which the second gain is approximately 0.08.

37. The system of claim 31, in which at least one of the first gain, the second gain, and the input threshold voltage is programmable.

38. The system of claim 31, in which the sense amplifier is coupled to the first and second electrodes during time periods during which the pacing pulses are delivered to the heart.

39. The system of claim 38, in which the sense amplifier is always coupled to the first and second electrodes.

40. The system of claim 31, in which the sense amplifier is directly connected to the first and second electrodes.

41. The system of claim 31, in which the sense amplifier is coupled to the first and second electrodes during time periods that are immediately after the time periods during which the pacing pulses are delivered to the heart.

42. The system of claim 31, in which the sense amplifier is coupled to the first and second electrodes during recharge time periods following the time periods during which the pacing pulses are delivered to the heart.

43. The system of claim 31, further comprising an amplitude measurement module, coupled to the first and second electrodes for measuring the amplitude of the pacing pulses.

44. The system of claim 31, further including an evoked response detection module having an input and an output, the input coupled to the first and second electrodes, the evoked response detection module determining, based on the sensed signal, whether the pacing pulse evoked an electrical depolarization of the heart.

45. The system of claim 44, further comprising an auto-capture module coupled the evoked response detection module and the therapy module for adjusting the amplitude of the pacing pulses based on the output of the evoked response detection module.

\* \* \* \* \*